(12) United States Patent
Dakka et al.

(10) Patent No.: US 8,445,730 B2
(45) Date of Patent: *May 21, 2013

(54) PROCESS FOR PRODUCING PHENOL

(75) Inventors: Jihad M. Dakka, Whitehouse Station, NJ (US); Kun Wang, Bridgewater, NJ (US); Edmund J. Mozeleski, Califon, NJ (US); Stephen Zushma, Clinton, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/061,601

(22) PCT Filed: Jul. 14, 2009

(86) PCT No.: PCT/US2009/050489
§ 371 (c)(1),
(2), (4) Date: Apr. 6, 2011

(87) PCT Pub. No.: WO2010/042261
PCT Pub. Date: Apr. 15, 2010

(65) Prior Publication Data
US 2011/0190546 A1 Aug. 4, 2011

Related U.S. Application Data

(60) Provisional application No. 61/104,292, filed on Oct. 10, 2008, provisional application No. 61/414,042, filed on Nov. 16, 2010.

(30) Foreign Application Priority Data

Dec. 17, 2008 (EP) ..................................... 08171948

(51) Int. Cl.
*C07C 409/00* (2006.01)
(52) U.S. Cl.
USPC ............ 568/573; 568/558; 568/568; 568/569
(58) Field of Classification Search
None
See application file for complete search history.

(56) References Cited

U.S. PATENT DOCUMENTS

| | | | |
|---|---|---|---|
| 3,821,314 A | 6/1974 | Arkell et al. | |
| 3,959,381 A | 5/1976 | Arkell et al. | |
| 4,021,490 A | 5/1977 | Hudson | |
| 4,230,638 A | 10/1980 | Murtha | |
| 4,262,151 A | 4/1981 | Pujado | |
| 4,358,618 A | 11/1982 | Sifniades et al. | |
| 4,480,141 A | 10/1984 | Drake | |
| 4,482,757 A | 11/1984 | Drake | |
| 4,487,970 A | 12/1984 | Drake | |
| 4,490,565 A | 12/1984 | Chang et al. | |
| 4,490,566 A | 12/1984 | Chang et al. | |
| 4,870,217 A | 9/1989 | Knifton | |
| 4,898,995 A | 2/1990 | Knifton et al. | |
| 5,254,751 A | 10/1993 | Zakoshansky | |
| 6,037,513 A | 3/2000 | Chang et al. | |
| 6,169,215 B1* | 1/2001 | Levin et al. | 568/798 |
| 6,284,927 B1 | 9/2001 | Druliner et al. | |
| 6,720,462 B2* | 4/2004 | Kuhnle et al. | 568/768 |
| 6,852,893 B2 | 2/2005 | Kuhnle et al. | |
| 2003/0083527 A1 | 5/2003 | Kuhnle et al. | |
| 2004/0162446 A1 | 8/2004 | Black | |
| 2004/0236152 A1 | 11/2004 | Black et al. | |
| 2007/0265476 A1 | 11/2007 | Dakka et al. | |

FOREIGN PATENT DOCUMENTS

| | | |
|---|---|---|
| EP | 0 492 807 | 7/1992 |
| GB | 681 613 | 10/1952 |
| WO | 2006/015826 | 2/2006 |
| WO | 2008/128638 | 10/2008 |

OTHER PUBLICATIONS

V. Zakoshansky, "*Acid-catalytic Cumene Hydroperoxide Cleavage Process in Boiling Acetone Medium*", presented at the AICHE Spring Meeting (Mar. 2002), New Orleans, LA.

R. Schmidt et al., "*New Developments in the Sunoco/UOP Phenol Technology*", presented at the AICHE Spring Meeting (Apr. 2004), New Orleans, LA.

G. Maksimov et al., "$WO^3/MO^2$ (=Zr, Sn, Ti) *Heterogeneous Acid Catalysts: Synthesis, Study, and Use in Cumene Hydroperoxide Decomposition*", Kinetics and Catalysis, 2006, vol. 47, No. 4, pp. 564-571.

J. Knifton et al., "*Phenol/Acetone Cogeneration Via Solid Acid Catalysis*", Applied Catalysis A: General, 1997, vol. 161, pp. 199-211.

R. Selvin et al., "*Catalytic Decomposition of Cumene Hydroperoxide into Phenol and Acetone*", Applied Catalysis A: General, 2001, vol. 219, pp. 125-129.

Y. Aoki et al., "*One-Pot Synthesis of Phenol and Cyclohexanone From Cycloheylbenzene Catalyzed by N-Hydroxyphthalimide (NHPI)*", Tetrahedron, 2005, vol. 61, pp. 5219-5222.

\* cited by examiner

*Primary Examiner* — Sudhakar Katakam
(74) *Attorney, Agent, or Firm* — Anthony G. Boone; Jamie L. Sullivan; Siwen Chen

(57) ABSTRACT

In a process for producing phenol or a substituted phenol, an alkylaromatic hydroperoxide having a general formula (I):

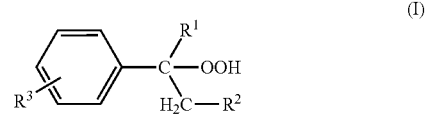

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, is contacted with a catalyst comprising an oxide of at least one metal from Groups 3 to 5 and Groups 7 to 14 of the Periodic Table of the Elements and an oxide of at least one metal from Group 6 of the Periodic Table of the Elements.

18 Claims, 3 Drawing Sheets

US 8,445,730 B2

PROCESS FOR PRODUCING PHENOL

PRIORITY CLAIM

This application is a National Stage Application of International Application No. PCT/US2009/050489 filed Jul. 14, 2009, which claims the benefit of prior U.S. provisional application Ser. No. 61/104,292 filed Oct. 10, 2008, both of which are hereby incorporated by reference in their entirety.

CROSS-REFERENCE TO RELATED APPLICATIONS

This application is related to U.S. provisional application Ser. No. 61/414,042, filed Nov. 16, 2010 and International Patent Cooperation Treaty Application No. PCT/EP2010/021949, filed Jan. 25, 2010.

FIELD

The present invention relates to a process for producing phenol or a substituted phenol.

BACKGROUND

Phenol is an important product in the chemical industry. For example, phenol is useful in the production of phenolic resins, bisphenol A, ε-caprolactam, adipic acid, alkyl phenols, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the cumene hydroperoxide. The product comprises equimolar amounts of phenol and acetone. However, the world demand for phenol is growing more rapidly than that for acetone. In addition, due to developing shortages in supply, the cost of propylene is likely to increase.

Thus, a process that avoids or reduces the use propylene as a feed and coproduces higher ketones, such as methyl ethyl ketone and/or cyclohexanone, rather than acetone may be an attractive alternative route to the production of phenol. For example, methyl ethyl ketone is in demand for use as a lacquer and a solvent and for dewaxing of lubricating oils. In addition, there is a growing market for cyclohexanone, which is used as an industrial solvent, as an activator in oxidation reactions and in the production of adipic acid, cyclohexanone resins, cyclohexanone oxime, caprolactam and nylon 6.

It is known that phenol and methyl ethyl ketone can be co-produced by a variation of the Hock process in which sec-butylbenzene is oxidized to obtain sec-butylbenzene hydroperoxide and the hydroperoxide is decomposed to the desired phenol and methyl ethyl ketone. The sec-butylbenzene can be produced by alkylation of benzene with linear butenes over zeolite beta or a molecular sieve of the MCM-22 family. Details of such a process can be found in, for example, International Patent Publication No. WO2006/015826.

Similarly, U.S. Pat. No. 6,037,513 discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt and mixtures thereof. The '513 patent also discloses that the resultant cyclohexylbenzene can be oxidized to the corresponding hydroperoxide and the peroxide decomposed to the desired phenol and cyclohexanone.

However, the production of phenol using sec-butylbenzene and/or cyclohexylbenzene as the alkylbenzene precursor is accompanied by certain problems which either are not present or are less severe with a cumene-based process. For example, in comparison to cumene, oxidation of sec-butylbenzene and cyclohexylbenzene to the corresponding hydroperoxide is very slow in the absence of a catalyst and is very sensitive to the presence of impurities. As a result, U.S. Pat. Nos. 6,720,462 and 6,852,893 have proposed the use of cyclic imides, such as N-hydroxyphthalimide, as catalysts to facilitate the oxidation of alkylbenzenes, such as sec-butylbenzene and cyclohexylbenzene.

With regard to the hydroperoxide cleavage step, current commercial phenol/acetone processes almost exclusively use a sulfuric acid catalyst, despite the fact that this yields phenol selectivities of only 92 to 96% of theoretical. The most common side reactions in sulfuric acid catalyzed cumene hydroperoxide cleavage include: 1) dehydration of carbinols (by-product from oxidation) forming α-methylstyrene, which can alkylate phenol forming heavy products and reducing the yield of phenol; 2) aldol condensation of ketone reducing ketone yield; and 3) oligomerization of olefins forming oligomers, all of which contribute to high boiling residue ("phenol tar") formation in the final product separate step. As a result, cumene hydroperoxide cleavage is generally carried out in multiple steps to reduce "phenol tar" formation. In addition, the sulfuric acid has to be properly neutralized after the cleavage step to avoid further reactions of the cleavage products.

All of these problems increase the complexity and investment involved in the cleavage process and hence various alternatives to sulfuric acid have been proposed for the production of phenol from cumene hydroperoxide. For example, other homogeneous acid catalysts, such as perchloric acid, phosphoric acid, toluenesulfonic acid and $SO_2$, have also been shown to be effective. However, all of these homogeneous catalysts suffer from the same downstream acid neutralization and product purification problems as sulfuric acid. To minimize these problems, various solid acid catalysts have been proposed for the heterogeneous cleavage of cumene hydroperoxide. For example, U.S. Pat. No. 4,490,565 discloses the use of zeolite beta in the cleavage of cumene hydroperoxide, whereas U.S. Pat. No. 4,490,566 discloses the use of a Constraint Index 1-12 zeolite, such as ZSM-5, and EP-A-492807 discloses the use of faujasite in the same process. The use of smectite clays in the acid-catalyzed decomposition of cumene hydroperoxide is described in U.S. Pat. No. 4,870,217.

U.S. Pat. No. 4,898,995 discloses a process for the coproduction of phenol and acetone by reacting cumene hydroperoxide over a heterogeneous catalyst consisting of either an ion exchange resin having sulfonic acid functionality or a heteropoly acid, such as 12-tungstophosphoric acid, on an inert support, such as silica, alumina, titania and zirconia. Such heteropoly acid catalysts are generally used as their hydrates, and as such are inherently unstable at temperatures in excess of 350° C.

U.S. Pat. No. 6,169,215 discloses process for producing phenol and acetone from cumene hydroperoxide, wherein said process comprises the step of contacting cumene hydroperoxide with a solid-acid catalyst produced by calcining a source of a Group IVB metal oxide with a source of an oxyanion of a Group VIB metal at a temperature of at least 400° C. The Group IVB metal oxide is selected from zirconia and titania and the Group VIB metal oxyanion is selected from oxyanions of chromium, molybdenum and tungsten.

In the case of the production of phenol from other alkylbenzenes, such as sec-butylbenzene and/or cyclohexylbenzene, to date little research has been conducted on the hydroperoxide cleavage step, although most proposals focus on the use of sulfuric acid and similar homogeneous catalysts. It is, however, apparent that any viable cleavage method will have to address the fact that production of the hydroperoxide is likely to require the use of a catalyst, such as a cyclic imide, and hence the direct product of the oxidation step could well contain nitrogen compounds, which are known poisons for the acid catalysts typically used for the cleavage step.

According to the present invention, it has now been found that certain mixed metal oxides are highly active catalysts for the cleavage of the hydroperoxides of higher alkylbenzenes and are capable of producing phenol with selectivities of 98% and higher. Moreover, although it may be desirable to remove the nitrogen impurities resulting from the catalyst used in producing the hydroperoxide, it has also been found that poisoning of the catalyst by such nitrogen impurities can be mitigated by diluting the hydroperoxide with a polar solvent and that the poisoned catalyst can be effectively rejuvenated by washing with a polar solvent. In addition, since the catalyst is a solid, the downstream neutralization and purification problems inherent with homogeneous catalysts, such as sulfuric acid, are avoided.

SUMMARY

In one aspect, the invention resides in a process for producing phenol or a substituted phenol, the process comprising contacting an alkylaromatic hydroperoxide having a general formula (I):

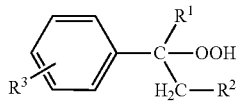

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with a catalyst comprising an oxide of at least one metal from Groups 3 to 5 and Groups 7 to 14 of the Periodic Table of the Elements and an oxide of at least one metal from Group 6 of the Periodic Table of the Elements.

Conveniently, the catalyst comprises an oxide of at least one metal from Group 4 of the Periodic Table of the Elements and an oxide of at least one metal from Group 6 of the Periodic Table of the Elements. In one embodiment, the catalyst comprises zirconium oxide and an oxide of molybdenum and/or tungsten.

Conveniently, the catalyst further comprises an oxide of at least one metal from Groups 8 to 11 of the Periodic Table of the Elements. In one embodiment, the catalyst further comprises an oxide of iron and/or copper.

Conveniently, said alkylaromatic hydroperoxide of general formula (I) is selected from sec-butylbenzene hydroperoxide, p-methyl-sec-butylbenzene hydroperoxide, 1,4-diphenylcyclohexane hydroperoxide, sec-pentylbenzene hydroperoxide, sec-hexylbenzene hydroperoxide, cyclopentylbenzene hydroperoxide, cyclohexylbenzene hydroperoxide and cyclooctylbenzene hydroperoxide. In one embodiment, the alkylaromatic hydroperoxide of general formula (I) is selected from sec-butylbenzene hydroperoxide and cyclohexylbenzene hydroperoxide.

Conveniently, said alkylaromatic hydroperoxide is dissolved in a polar solvent.

Conveniently, said contacting is conducted at a temperature of about 40° C. to about 120° C., a pressure of about 100 to about 1000 kPa, and a liquid hourly space velocity (LHSV) based on the hydroperoxide of about 1 to about 50 $hr^{-1}$.

In a further aspect, the invention resides in a process for producing phenol or a substituted phenol, the process comprising:

(a) contacting an alkylaromatic compound having a general formula (II):

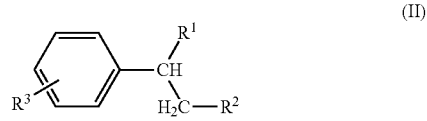

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with an oxygen-containing gas in the presence of a catalyst comprising a cyclic imide having a general formula (III):

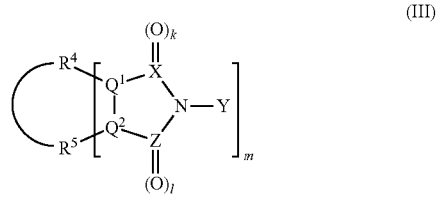

wherein each of $R^4$ and $R^5$ is independently selected from hydrocarbyl and substituted hydrocarbyl radicals having 1 to 20 carbon atoms, or from the groups $SO_3H$, $NH_2$, OH, and $NO_2$ or from the atoms H, F, Cl, Br, and I, provided that $R^4$ and $R^5$ can be linked to one another via a covalent bond;
each of $Q^1$ and $Q^2$ is independently selected from C, CH, N, $CR^6$;
each of X and Z is independently selected from C, S, $CH_2$, N, P and elements of Group 4 of the Periodic Table;
Y is O or OH;
k is 0, 1, or 2;
l is 0, 1, or 2;
m is 1 to 3; and
$R^6$ can be any of the entities listed for $R^4$, and wherein said contacting is conducted under conditions to convert said alkylaromatic compound to an alkylaromatic hydroperoxide having a general formula (I):

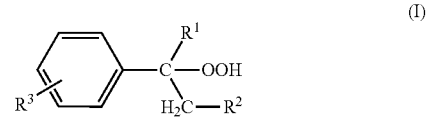

in which each of $R^1$, $R^2$ and $R^3$ are as defined above; and (b) contacting said alkylaromatic hydroperoxide with an oxide catalyst comprising an oxide of at least one metal from Groups 3 to 5 and Groups 7 to 14 of the Periodic Table of the Elements and an oxide of at least one metal from Group 6 of the Periodic Table of the Elements.

Conveniently, said cyclic imide obeys the general formula (IV):

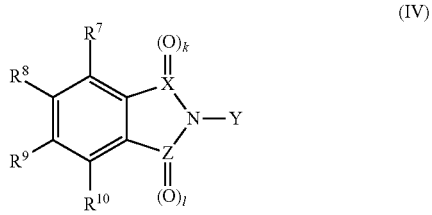

wherein each of $R^7$, $R^8$, $R^9$, and $R^{10}$ is independently selected from hydrocarbyl and substituted hydrocarbyl radicals having 1 to 20 carbon atoms, or from the groups $SO_3H$, $NH_2$, OH, and $NO_2$ or from the atoms H, F, Cl, Br, and I, each of X and Z is independently selected from C, S, $CH_2$, N, P and elements of Group 4 of the Periodic Table;
Y is O or OH;
k is 0, 1, or 2; and
l is 0, 1, or 2.

In one embodiment, said cyclic imide comprises N-hydroxyphthalimide.

Conveniently, said contacting (a) produces an effluent comprising said alkylaromatic hydroperoxide and unreacted cyclic imide catalyst and the process further comprises:

(c) treating said effluent prior to said contacting (b) to remove at least part of the unreacted cyclic imide catalyst in said effluent.

In one embodiment, said treating (c) comprises contacting said effluent with an aqueous solution of a base, conveniently having a pKb value greater than or equal to the pKa value of the cyclic imide, to produce an aqueous phase comprising at least part of said unreacted imide catalyst and an organic phase comprising said alkylaromatic hydroperoxide.

In another embodiment, said treating (c) comprises contacting said effluent with a solid sorbent, such as comprises a metal oxide, a metal carbonate and/or hydrogen carbonate, clay, and/or an ion exchange resin.

Conveniently, the process further comprises periodically rejuvenating said oxide catalyst by washing the oxide catalyst with a polar solvent, such as acetone.

DETAILED DESCRIPTION OF THE EMBODIMENTS

Figure 1:
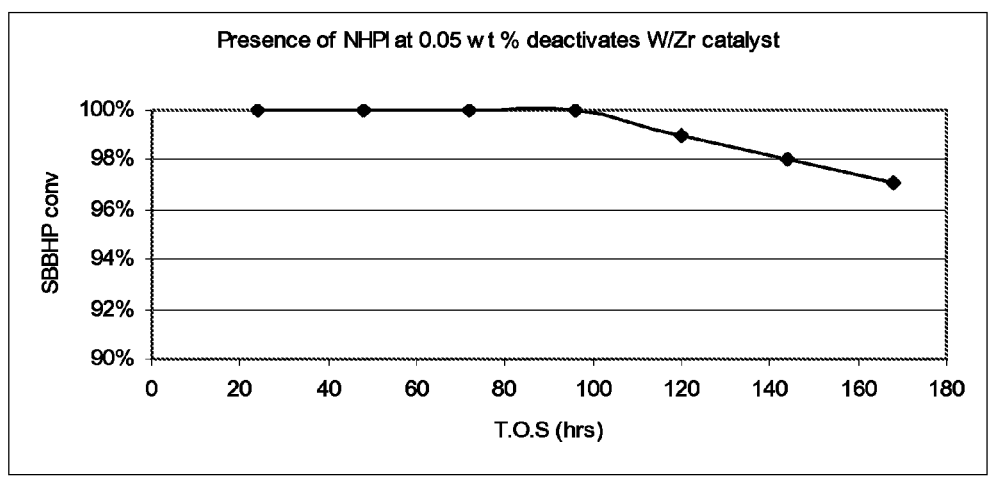
FIG. 1 is a graph of sec-butylbenzene hydroperoxide conversion against time on stream for the cleavage of sec-butylbenzene hydroperoxide over a Fe/W/Zr oxide catalyst according to the process of Example 9.

Described herein is a process for producing phenol or a substituted phenol, wherein the process comprises contacting an alkylaromatic hydroperoxide having the general formula (I):

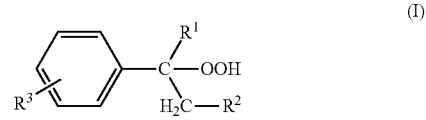

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with a mixed metal oxide catalyst.

Examples of suitable alkylaromatic hydroperoxides include sec-butylbenzene hydroperoxide, p-methyl-sec-butylbenzene hydroperoxide, 1,4-diphenylcyclohexane hydroperoxide, sec-pentylbenzene hydroperoxide, sec-hexylbenzene hydroperoxide, cyclopentylbenzene hydroperoxide, cyclohexylbenzene hydroperoxide and cyclooctylbenzene hydroperoxide. Preferred alkylaromatic hydroperoxides of general formula (I) include sec-butylbenzene hydroperoxide and cyclohexylbenzene hydroperoxide.

Production of Alkylaromatic Hydroperoxides

The alkylaromatic hydroperoxides employed in the present process are typically produced by the catalyzed oxidation of an alkylaromatic compound having the general formula (II):

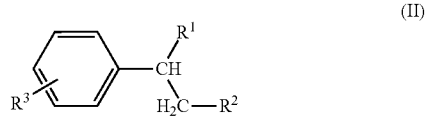

wherein $R^1$, $R^2$ and $R^3$ have the meanings ascribed in the above definition of formula (I). The alkylaromatic precursor compound is in turn produced by known aromatic alkylation processes. For example, sec-butylbenzene hydroperoxide is conveniently produced by oxidation of the sec-butylbenzene product resulting from the alkylation of benzene with linear butenes in presence of an MCM-22 family catalyst, such as described in International Patent Publication No. WO2006/015826. Similarly, cyclohexylbenzene hydroperoxide is conveniently produced by oxidation of the cyclohexylbenzene product resulting from the hydroalkylation of benzene in presence of bifunctional catalyst comprising an MCM-22 family molecular sieve and a hydrogenation metal, such as described in U.S. Pat. No. 6,037,513. Similar processes can be used to produce the other hydroperoxides that can be employed in the present process.

The oxidation process employed in the production of the desired hydroperoxide generally involves reacting the alkylaromatic precursor with an oxygen-containing gas in the presence of a catalyst comprising a cyclic imide having a general formula (III):

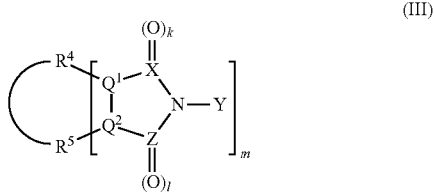

wherein each of $R^4$ and $R^5$ is independently selected from hydrocarbyl and substituted hydrocarbyl radicals having 1 to 20 carbon atoms, or from the groups $SO_3H$, $NH_2$, OH, and $NO_2$ or from the atoms H, F, Cl, Br, and I, provided that $R^4$ and $R^5$ can be linked to one another via a covalent bond;

each of $Q^1$ and $Q^2$ is independently selected from C, CH, N, $CR^6$;

each of X and Z is independently selected from C, S, $CH_2$, N, P and elements of Group 4 of the Periodic Table;

Y is O or OH;

k is 0, 1, or 2;

l is 0, 1, or 2;

m is 1 to 3; and $R^6$ can be any of the entities listed for $R^4$, and wherein said contacting is conducted under conditions to convert the alkylaromatic compound to the desired hydroperoxide.

Conveniently, the cyclic imide obeys the general formula (IV):

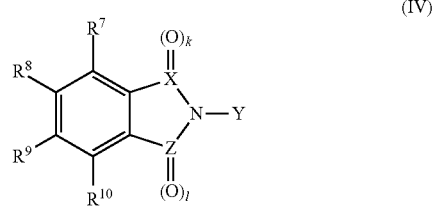

wherein each of $R^7$, $R^8$, $R^9$, and $R^{10}$ is independently selected from hydrocarbyl and substituted hydrocarbyl radicals having 1 to 20 carbon atoms, or from the groups $SO_3H$, $NH_2$, OH, and $NO_2$ or from the atoms H, F, Cl, Br, and I, each of X and Z is independently selected from C, S, $CH_2$, N, P and elements of Group 4 of the Periodic Table;

Y is O or OH;

k is 0, 1, or 2; and l is 0, 1, or 2.

In one practical embodiment, the cyclic imide comprises N-hydroxyphthalimide.

Suitable conditions for the oxidation step include a temperature between about 70° C. and about 200° C., such as about 90° C. to about 130° C., and a pressure of about 0.5 to about 20 atmospheres (50 to 2000 kPa). The oxidation reaction is conveniently conducted in a catalytic distillation unit and the per-pass conversion is preferably kept below 50%, to minimize the formation of byproducts.

The oxidation step converts the alkylaromatic precursor compound to its associated hydroperoxide. However, the oxidation process also tends to generate water and organic acids (e.g., acetic or formic acid) as by-products, which can hydrolyse the catalyst and also lead to decomposition of the hydroperoxide species. Thus, in one embodiment, the conditions employed in the oxidation step, particularly the pressure and oxygen concentration, are controlled so as to maintain the concentration of water and organic acids in the reaction medium below 50 ppm. Such conditions typically include conducting the oxidation at relatively low pressure, such as below 300 kPa, for example between about 100 kPa and about 200 kPa. Moreover, although the oxidation can be conducted over a broad oxygen concentration range between 0.1 and 100%, it is preferred to operate at relatively low oxygen concentration, such as no more than 21 volume %, for example from about 0.1 to about 21 volume %, generally from about 1 to about 10 volume %, oxygen in the oxygen-containing gas. In addition, maintaining the desired low levels of water and organic acids is facilitated by passing a stripping gas through the reaction medium during the oxidation step.

In one embodiment, the stripping gas is the same as the oxygen-containing gas. In another embodiment, the stripping gas is different from the oxygen-containing gas and is inert to the reaction medium and the cyclic imide catalyst. Suitable stripping gases include inert gases, such as helium and argon.

An additional advantage of operating the oxidation process at low pressure and low oxygen concentration and by stripping water and organic acids, from the reaction medium is that light hydroperoxide (e.g., ethyl or methyl hydroperoxide), light ketones (e.g., methyl ethyl ketone), light aldehydes (e.g., acetaldehyde) and light alcohols (e.g., ethanol) are removed from the reaction products as they are formed. Thus light hydroperoxides are hazardous and pose a safety concern if their concentration in the liquid product becomes too high. Also, light hydroperoxides, alcohols, aldehydes and ketones are precursors for the formation of organic acids and water so that removing these species from the oxidation medium improves the oxidation reaction rate and selectivity and the stability of the cyclic imide catalyst. In fact, data shows that when conducting oxidation of sec-butylbenzene with NHPI at 100 psig (790 kPa), more than 99 mol % of these light species and water remain in the reactor, whereas at atmospheric pressure, more than 95 mol % of these species are removed from the oxidation reactor.

The product of the oxidation reaction includes the desired alkyl hydroperoxide together with unreacted alkylaromatic precursor and unreacted cyclic imide catalyst. The unreacted alkylaromatic precursor is readily removed by distillation and recycled to the oxidation step. However, as will be discussed below, the unreacted cyclic imide catalyst can act as a poison to the downstream mixed metal oxide catalyst employed to cleave the hydroperoxide into phenol. Moreover, the cyclic imide tends to be expensive, making it desirable to recover and recycle the unreacted catalyst. Thus, it will normally be desirable to treat the effluent from the oxidation process to reduce the level of unreacted cyclic imide prior to passage of the effluent to the cleavage step.

In one embodiment, treatment of the oxidation effluent comprises contacting the effluent with an aqueous solution of a base, particularly a weak base having a pKb value greater than or equal to the pKa of the cyclic imide catalyst, whereby the unreacted imide catalyst is extracted into the aqueous phase, leaving an organic phase which comprises said oxidized hydrocarbon product and which contains a reduced level of cyclic imide. Generally, the extraction is conducted so as to reduce the level of the imide in the organic phase to less than 100 ppm, such as less than 50 ppm, for example less than 10 ppm, by weight of the organic phase.

The use of a weak base in the extraction of the unreacted imide catalyst is generally desirable since a weak base is less likely to catalyze decomposition of the imide after extraction into the aqueous phase. A suitable weak base includes a metal carbonate and/or hydrogen carbonate, especially an alkali metal carbonate and/or hydrogen carbonate, such as sodium carbonate.

The conditions used in the cyclic imide extraction step need not be closely controlled but generally include a temperature of about 10° C. to about 80° C., such as about 20° C. to about 70° C. The time of extraction may be for example from about 1 minute to about 30 minutes, such as about 5 minutes to about 10 minutes. The amount of base employed in the extraction step is normally sufficient to provide at least an equimolar quantity of base to unreacted imide, such as 1 to 3 moles of base per mole of unreacted imide. Generally, the phases are agitated during extraction to maximize contact between the phases.

After extraction into the aqueous base solution, the unreacted cyclic imide can readily be recovered by acidifying the aqueous phase, for example with acetic acid, to precipitate the unreacted imide. After separation from the aqueous phase, for example by filtration or centrifugation, the precipitated unreacted imide may, if desired, be recycled to the oxidation step.

In another embodiment, treatment of the oxidation effluent comprises contacting the effluent with a solid sorbent, which is effective to remove some or substantially all of the unreacted imide catalyst, so as to produce a treated effluent which is rich in said oxidized hydrocarbon product and which contains a reduced or zero level of cyclic imide. Again, the sorption process is conducted so as to reduce the level of the imide in the organic phase to less than 100 ppm, such as less than 50 ppm, for example less than 10 ppm, of the organic phase.

Suitable solid sorbents are those having basic properties, including metal carbonates and/or hydrogen carbonates, which may be provided on a porous support, clays, ion exchange resins and metal oxides, particularly mixed metal oxides.

Metal oxides having sufficient basic properties to be effective sorbents in the cyclic imide extraction step may be determined by the molar ratio of chemisorption of $CO_2$ and $NH_3$ over these metal oxide materials. $CO_2$, a mild acid, is used to titrate the basic sites present on the metal oxide being tested. Likewise, $NH_3$, a strong base, is titrated to indicate the acidic sites on the material. Many factors determine the actual amount of chemisorption such as surface area of the material (often significantly affected by the metal oxide preparation method), the temperature at which the chemisorption is tested, and the pressure at which the chemisorption is tested. For the present purposes, a "basic" oxide is defined as an oxide having a molar ratio of chemisorption of $CO_2$ per gram of metal oxide to the chemisorption of $NH_3$ per gram of metal oxide greater than 0.5, typically greater than 0.75, and especially greater than 1.0, when tested as described below.

Testing to determine the molar ratio of chemisorption of $CO_2$ per gram of metal oxide to the chemisorption of $NH_3$ per gram of metal oxide is conducted using a Mettler TGA/SDTA 851 thermogravimetric analysis system at ambient pressure. The metal oxide sample is calcined in flowing air to about 500° C. (except as noted in Table 1) for about three hours; at least until a constant sample weight is obtained. The temperature of the sample is then reduced in flowing air (helium could also be used) to the desired temperature of chemisorption. Next, the sample is allowed to equilibrate at the desired temperature in flowing helium and weighed. Chemisorption of carbon dioxide is measured at 100° C., and chemisorption of ammonia is measured at 250° C. After being weighed, the sample is subjected to a number of pulses (about 12 seconds/pulse) of gaseous mixture containing helium and either carbon dioxide or ammonia until a constant weight was obtained. The gas mixture contains about 10 weight percent carbon dioxide or ammonia with the remainder being helium. After each pulse of the gas mixture being tested, the metal oxide sample is flushed with flowing helium for about 3 minutes. About 20 separate pulses of the gas mixture is used in each test. The increase in weight of the sample in terms of mg/g metal oxide based on the metal oxide sample weight after calcination is used to determine the moles of $CO_2$ or $NH_3$ adsorbed per gram of metal oxide.

Molar ratios of chemisorption of $CO_2$ to the chemisorption of $NH_3$ per gram of sorbate for some representative metal oxide species are shown in Table 1.

TABLE 1

| Material Tested | Calcination Temperature, ° C. | $CO_2/NH_3$ Chemisorption Molar Ratio |
|---|---|---|
| $TiO_2$ | 700 | 0.33 |
| $W/ZrO_2$ | 800 | 0.07 |
| $La_2O_3$ | 700 | 0.86 |
| $La/SiO_2$ | 500 | 0.92 |
| $AlPO_x$ | 500 | 0.75 |
| $NdAlPO_x$ | 500 | 1.04 |
| $YAlPO_x$ | 500 | 0.86 |
| $PrAlPO_x$ | 500 | 1.05 |
| MgO | 700 | 11.47 |
| $Y_2O_3$ | 700 | 14.95 |

Metal oxides suitable for use as solid sorbents in the cyclic imide extraction step include oxides and mixed oxides of metals of Group 2, Group 3, Group 4, Lanthanide Series, or Actinide Series of the Periodic Table. In one embodiment, the sorbent comprises two or more metal oxides, preferably one Group 4 metal oxide and one or more selected from Group 2, Group 3, Lanthanide Series, and Actinide Series metal oxides. The oxides can be prepared using a variety of methods, although generally are prepared by conversion of a suitable precursor by precipitation from solution and/or calcination. Suitable precursors include metal salts, such as halides, sulfates, phosphates, halides, nitrates, oxychlorides, alkoxides and acetates.

In one embodiment, the metal oxide is produced by first preparing a liquid solution comprising a salt of the metal in a solvent, such as water. The resultant solution is then subjected to conditions sufficient to cause precipitation of the solid oxide material, such as by the addition of a precipitating reagent, typically a base such as sodium hydroxide or ammonium hydroxide. The liquid solution is generally maintained at a temperature at or below 200° C. during the precipitation, for example in the range of from about 0° C. to about 200° C., such as from about 20° C. to about 100° C. The resulting gel is preferably then hydrothermally treated at a temperature of at least 80° C., preferably at least 100° C., for up to 10 days, such as up to 5 days, for example up to 3 days. The resulting material is then recovered, for example by filtration or centrifugation, washed, and dried. The resulting particulate material is typically then calcined, normally in an oxidizing atmosphere, at a temperature of at least 400° C., such as from about 400° C. to about 800° C., for up to 48 hours, such as for about 0.5 hours to about 24 hours, for example for about 1 hour to about 10 hours.

When two or more metal oxides are used in the cyclic imide extraction step, they may either be co-precipitated or precipitated separately and combined with each other at any later stage of processing including as calcined solid particles.

Suitable ion exchange resins for use as the solid sorbent include those resins conventionally employed for removing acidic or basic species, such as Amberlyst exchange resins.

Suitable conditions for the cyclic imide sorption with a solid sorbent include a temperature of about 10° C. to about 130° C., such as about 20° C. to about 80° C., for a time of about 1 minute to about 30 minutes, such as about 5 minutes to about 10 minutes.

After removal by the solid sorbent, the unreacted cyclic imide can readily be recovered by washing the sorbent with a polar solvent, for example with ethanol or acetone. The recovered imide can then be recycled to the oxidation step, with or without prior removal of the ethanol, since it is found that the presence of ethanol with the imide does not adversely affect the oxidation activity or selectivity of the recycled catalyst.

Hydroperoxide Cleavage

The hydroperoxide cleavage step of the present process is conducted by contacting the effluent from the oxidation step, normally after removal of the unreacted alkylaromatic precursor and optionally after pretreating the effluent to reduce the level of cyclic imide to less than 100 ppm, with a mixed metal oxide catalyst. In particular, the mixed metal oxide catalyst comprises an oxide of at least one metal from Groups 3 to 5 and Groups 7 to 14 of the Periodic Table of the Elements, conveniently an oxide of at least one metal from Group 4 of the Periodic Table of the Elements, and an oxide of at least one metal from Group 6 of the Periodic Table of the Elements. In one embodiment, the catalyst comprises zirconium oxide an oxide of molybdenum and/or tungsten.

Conveniently, the catalyst further comprises an oxide of at least one metal from Groups 8 to 11 of the Periodic Table of the Elements, such as an oxide of iron and/or copper.

The mixed metal oxide catalyst is conveniently prepared by combining a first liquid solution, such as an aqueous solution, comprising a source of ions of at least one metal from Groups 3 to 5 and Groups 7 to 14 with a second liquid solution, again such as an aqueous solution, comprising a source of ions of at least one Group 4 metal and optionally with a third solution comprising a source of ions of at least one Group 8 to 11 metal. This combination can take place under conditions sufficient to cause co-precipitation of a mixed oxide material as a solid from the liquid medium. Alternatively, the source of ions of the metal(s) from Groups 3 to 5 and Groups 7 to 14, the source of ions of the Group 4 metal and optionally the source of ions of the Group 8 to 11 metals may be combined into a single solution. This solution may then be subjected to conditions sufficient to cause co-precipitation of the solid mixed oxide material, such as by the addition of a precipitating reagent to the solution. Conveniently, the precipitation is conducted at a pH above 7. For example, the precipitating agent may be a base such as sodium hydroxide or ammonium hydroxide.

The temperature at which the liquid medium is maintained during the precipitation is generally less than about 200° C., such as in the range of from about 0° C. to about 200° C. A particular range of temperatures for precipitation is from about 20° C. to about 100° C. The resulting gel is preferably then hydrothermally treated at temperatures of at least 80° C., preferably at least 100° C. The hydrothermal treatment typically takes place in a vessel at atmospheric pressure. The gel, in one embodiment, is hydrothermally treated for up to 10 days, such as up to 5 days, for example up to 3 days.

The hydrated precursor to the mixed metal oxide is then recovered, for example by filtration or centrifugation, and washed and dried. The resulting material can then be calcined, such as in an oxidizing atmosphere, at a temperature of at least 400° C., such as at least 500° C., for example from about 600° C. to about 900° C., and particularly from about 650° C. to about 800° C., to form the mixed metal oxide catalyst. The calcination time is typically up to 48 hours, such as for about 0.5 to 24 hours, for example for about 1.0 to 10 hours. In one embodiment, calcination is carried out at about 700° C. for about 1 to about 3 hours.

The cleavage reaction is conveniently affected by contacting the hydroperoxide with the mixed metal oxide catalyst in the liquid phase at a temperature of about 20° C. to about 150° C., such as about 40° C. to about 120° C., and/or a pressure of about 50 to about 2500 kPa, such as about 100 to about 1000 kPa and/or a liquid hourly space velocity (LHSV) based on the hydroperoxide of about 0.1 to about 1000 $hr^{-1}$, preferably about 1 to about 50 $hr^{-1}$. The cleavage reaction is conveniently conducted in a catalytic distillation unit.

The hydroperoxide is typically diluted in an organic solvent inert to the cleavage reaction, such as methyl ethyl ketone, phenol, cyclohexylbenzene, cyclohexanone and sec-butylbenzene, to assist in heat removal. More preferably, alkylaromatic hydroperoxide is dissolved in a polar solvent, such as acetone, for the cleavage reaction since it is found that the presence of the polar solvent can mitigate the poisoning of the mixed metal oxide catalyst cleavage catalyst by cyclic imides remaining from the oxidation reaction.

Irrespective of the presence or absence of unreacted cyclic imide in the feed to the cleavage reaction it is found that the mixed metal oxide will tend to lose its activity over time, resulting in a decrease in the degree of conversion of the hydroperoxide to phenol. It is, however, found that the cleavage activity of the catalyst can be restored by periodically rejuvenating the catalyst by washing the catalyst with a polar solvent, such as acetone.

In the case where the alkylaromatic compound that is oxidized according to the invention is cyclohexylbenzene, the oxidation product comprises cyclohexylbenzene hydroperoxide and the cleavage product comprises phenol and cyclohexanone. The crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species. The crude or purified cyclohexanone may itself be subjected to dehydrogenation in order to convert it to phenol. Such dehydrogenation may be performed, for example, over a catalyst such as platinum, nickel or palladium.

The invention will now be more particularly described with reference to the following non-limiting Examples.

EXAMPLE 1

Synthesis of Mo/Zr Oxide Catalyst

Five hundred grams of $ZrOCl_2.8H_2O$ were dissolved with stirring in 3 liters of distilled water. Another solution containing 260 grams of concentrated ammonium hydroxide, 66 grams of $(NH_4)_6Mo_7O_{24}.4H_2O$ and 3 liters of distilled water was prepared. Both solutions were heated to 60° C. and the heated solutions were combined at a rate of 50 ml/min using nozzle mixing. The pH of the final composite was adjusted to approximately 9 by the addition of concentrated ammonium hydroxide. The resultant slurry was then put in polypropylene bottles and placed in a steambox (100° C.) for 72 hours. The product formed was recovered by filtration, washed with excess water, and dried overnight at 85° C. A sample of this catalyst was calcined to 800° C. in flowing air for 3 hours. The calcined catalyst contained 16% Mo by weight of the total weight Mo and Zr in the catalyst.

EXAMPLE 2

Synthesis of Cu/W/Zr Oxide Catalyst

Five hundred grams of $ZrOCl_2.8H_2O$ were dissolved with stirring in 3.0 liters of distilled water and 6.8 grams of $CuSO_4.5H_2O$ were added to this solution. Another solution containing 260 grams of concentrated ammonium hydroxide, 54 grams of $(NH_4)_6H_2W_{12}O_{40}.xH_2O$ and 3 liters of distilled water was prepared. Both solutions were heated to 40° C. and the heated solutions were combined at a rate of 50 ml/min using nozzle mixing. The pH of the final composite was adjusted to approximately 9 by the addition of concentrated ammonium hydroxide. The resultant slurry was then put in polypropylene bottles and placed in a steambox (100° C.) for 72 hours. The product formed was recovered by filtration, washed with excess water, and dried overnight at 85° C. A sample of this catalyst was calcined to 700° C. in flowing air for 3 hours. The calcined catalyst contained 1% Cu and 16% W by weight of the total weight W, Zr and Cu in the catalyst.

EXAMPLE 3

Synthesis of Fe/W/Zr Oxide Catalyst

One thousand grams of $ZrOCl_2.8H_2O$ were dissolved with stirring in 3.0 liters of distilled water and then 15.2 grams of $FeSO_4.7H_2O$ were added to this solution. Another solution containing 400 grams of concentrated ammonium hydroxide, 108 grams of $(NH_4)_6H_2W_{12}O_{40}.xH_2O$ and 2940 ml of distilled water was prepared. Both solutions were heated to 60° C. and the heated solutions were combined at a rate of 50 ml/min using nozzle mixing. The pH of the final composite was adjusted to approximately 9 by the addition of concentrated ammonium hydroxide. The resultant slurry was then put in polypropylene bottles and placed in a steambox (100° C.) for 72 hours. The product formed was recovered by filtration, washed with excess water, and dried overnight at 85° C. A sample of this catalyst was calcined to 800° C. in flowing air for 3 hours. The calcined catalyst had a surface area of 73 $m^2/g$ and contained 1% Fe and 16% W by weight of the total weight W, Zr and Fe in the catalyst.

EXAMPLE 4

Synthesis of W/Zr Oxide Catalyst

One thousand grams of $ZrOCl_2.8H_2O$ were dissolved with stirring in 3.0 liters of distilled water. Another solution containing 400 grams of concentrated ammonium hydroxide, 108 grams of $(NH_4)_6H_2W_{12}O_{40}.xH_2O$ and 3.0 liters of distilled water was prepared. Both solutions were heated to 60° C. and the heated solutions were combined at a rate of 50 ml/min using a nozzle mixing. The pH of the final composite was adjusted to approximately 9 by the addition of concentrated ammonium hydroxide. The resultant slurry was then put in polypropylene bottles and placed in a steambox (100° C.) for 72 hours. The product formed was recovered by filtration, washed with excess water, and dried overnight at 85° C. A sample of this catalyst was calcined to 800° C. in flowing air for 3 hours. The calcined catalyst had a surface area of 73 $m^2/g$ and contained 16% W by weight of the total weight W and Zr in the catalyst.

EXAMPLE 5

Synthesis of Fe/W/Zr Oxide Catalyst

Five hundred grams of $ZrOCl_2.8H_2O$ were dissolved with stirring in 3.0 liters of distilled water and then 7.6 grams of $FeSO_4.7H_2O$ were added to this solution. Another solution containing 260 grams of concentrated ammonium hydroxide, 54 grams of $(NH_4)_6H_2W_{12}O_{40}.xH_2O$ and 2940 ml of distilled water was prepared. Both solutions were heated to 60° C. and the heated solutions were combined at a rate of 50 ml/min using nozzle mixing. The pH of the final composite was adjusted to approximately 9 by the addition of concentrated ammonium hydroxide. The resultant slurry was then put in polypropylene bottles and placed in a steambox (100° C.) for 72 hours. The product formed was recovered by filtration, washed with excess water, and dried overnight at 85° C. A sample of this catalyst was calcined to 800° C. in flowing air for 3 hours. The calcined catalyst had a surface area of 71 $m^2/g$ and contained 1% Fe and 16% W by weight of the total weight W, Zr and Fe in the catalyst.

EXAMPLE 6

Cleavage of Cyclohexylbenzene Hydroperoxide Using Mo/Zr Oxide Catalyst of Example 1

The catalyst prepared in Example 1 was pelletized to 40-80 mesh size, mixed with 60-80 mesh sand (v/v 1:1), and loaded into a ¼-inch (0.6 cm) diameter stainless steel tubular reactor. The reactor was held at 70° C. and liquid acetone was passed through the reactor tube at 3 cc/min via an ISCO pump for 30 min. The acetone feed was turned off and a 5 wt % solution of cyclohexylbenzene hydroperoxide in acetone was fed to the reactor via another ISCO pump at a rate of 0.45 cc/min. The products were collected in a chilled knock-out pot and sampled for GC analysis periodically. At the completion of the run, a different cyclohexylbenzene hydroperoxide flow rate was used to change the residence time.

EXAMPLE 7

Cleavage of Cyclohexylbenzene Hydroperoxide Using Cu/W/Zr Oxide Catalyst of Example 2

The catalyst prepared in Example 2 was pelletized to 40-80 mesh size, mixed with 60-80 mesh sand (v/v 1:1), and loaded into a ¼-inch (0.6 cm) diameter stainless steel tubular reactor. The reactor was held at 70° C. and liquid acetone was passed through the reactor tube at 3 cc/min via an ISCO pump for 30 min. The acetone feed was turned off and a 5 wt % solution of cyclohexylbenzene hydroperoxide in acetone was fed to the reactor via another ISCO pump at a rate of 0.45 cc/min. The products were collected in a chilled knock-out pot and sampled for GC analysis periodically. At the completion of the run, a different cyclohexylbenzene hydroperoxide flow rate was used to change the residence time.

EXAMPLE 8

Cleavage of Cyclohexylbenzene Hydroperoxide Using Fe/W/Zr Oxide Catalyst of Example 3

The catalyst prepared in Example 3 was pelletized to 40-80 mesh size, mixed with 60-80 mesh sand (v/v 1:1), and loaded into a ¼-inch (0.6 cm) diameter stainless steel tubular reactor. The reactor was held at 70° C. and liquid acetone was passed through the reactor tube at 3 cc/min via an ISCO pump for 30 min. The acetone feed was turned off and a 5 wt % solution of cyclohexylbenzene hydroperoxide in acetone was fed to the reactor via another ISCO pump at a rate of 0.45 cc/min. The products were collected in a chilled knock-out pot and sampled for GC analysis periodically. At the completion of the run, a different cyclohexylbenzene hydroperoxide flow rate was used to change the residence time.

The results for Examples 6 to 8 are shown in Table 1, from which it will be seen that the mixed metal oxides of Examples 1 to 3 are very active and selective catalysts for the cleavage of cyclohexylbenzene hydroperoxide (CHBHP) into phenol and cyclohexanone.

TABLE 2

| Example | Residence time (min) | CHBHP conv. (%) | 4-Phenyl-cyclohexanol conv. (%) | 1-Phenyl-cyclohexanol conv. (%) | Phenol yield (%) | Cyclohexanone yield (%) |
| --- | --- | --- | --- | --- | --- | --- |
| 6 | 1 | 98.8 | 56.7 | 100 | 98 | 98 |
|   | 0.5 | 98.8 | 56.3 | 100 | 98 | 98 |
|   | 0.3 | 98.8 | 56.7 | 100 | 98 | 98 |
|   | 0.225 | 98.8 | 56.1 | 100 | 98 | 98 |
| 7 | 1 | 98.9 | 60.3 | 100 | 98 | 98 |
|   | 0.5 | 98.9 | 59.9 | 100 | 98 | 98 |
|   | 0.3 | 98.9 | 56.6 | 89.3 | 98 | 98 |
|   | 0.225 | 98.5 | 53.1 | 83.8 | 98 | 98 |
| 8 | 1 | 99.1 | 51.8 | 100 | 99 | 99 |
|   | 0.5 | 99.0 | 51.7 | 100 | 99 | 99 |
|   | 0.3 | 99.0 | 53.9 | 100 | 99 | 99 |
|   | 0.225 | 99.0 | 54.1 | 94.1 | 99 | 99 |
| Sand | 1 | 27 | 0 | 0 | 67 | 66 |

EXAMPLE 9

Sec-Butylbenzene Hydroperoxide Cleavage over Fe/W/Zr Oxide Catalyst of Example 5—NHPI in Feed Not Removed The catalyst (1.5 g) prepared in Example 5 was pelletized to 20-40 mesh size, mixed with 60-80 mesh sand (1.5 g) (v/v 1:1), and loaded into a ⅜-inch (1 cm) diameter stainless steel tubular reactor. The reactor was heated to 90° C. and held at 90° C. with liquid methyl ethyl ketone (MEK) introduction through the reactor tube at 1 cc/min via an ISCO pump for 135 min. The MEK feed was turned off and a 5 wt % solution of sec-butylbenzene hydroperoxide (SBBHP) in MEK was introduced to the reactor via another ISCO pump at a rate of 0.25 cc/min. The sec-butylbenzene hydroperoxide had been produced by the oxidation of sec-butylbenzene in the presence of 0.11 wt % of a N-hydroxyphthalimide catalyst without removal of the catalyst prior to dissolving the hydroperoxide in MEK and feeding the solution to the cleavage reactor. Thus the SBBHP/MEK solution fed to the cleavage step contained 500 ppm of unreacted N-hydroxyphthalimide catalyst. The products of the cleavage reaction were collected in a chilled knock-out pot and sampled for GC analysis. The results are shown in FIG. 1, which shows that the catalyst started to deactivate after about 95 hrs of time on stream, as indicated by the decrease of SBBHP conversion.

EXAMPLE 10

Figure 2:
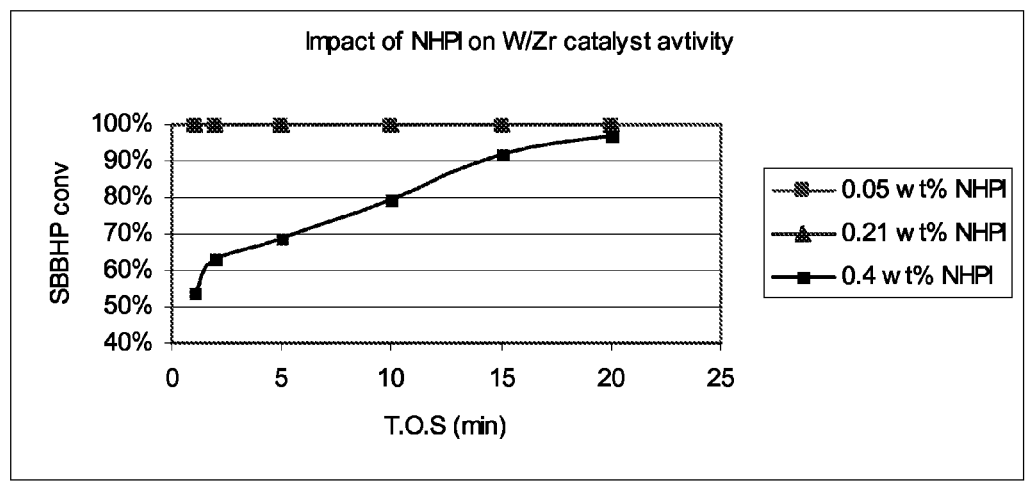
FIG. 2 is a graph of sec-butylbenzene hydroperoxide conversion against time on stream for the cleavage of sec-butylbenzene hydroperoxide over a Fe/W/Zr oxide catalyst in the presence of varying amounts of N-hydroxyphthalimide according to the process of Example 10.

Sec-Butyl Hydroperoxide Cleavage Over Fe/W/Zr Oxide Catalyst of Example 5—Effect of NHPI Concentration in Feed Into a 3-necked 100 ml round bottom flask equipped with an air stirrer, thermometer, chilled water cooled condenser, and nitrogen inductor were added acetone (39.5 g, 50 ml) and 0.5 g of powdered catalyst of Example 5. The acetone and catalyst were heated under acetone reflux (56° C.), and, while refluxing, 10 cc (10.42 g) of 70 wt. % sec-butylbenzene hydroperoxide concentrate containing 0.05 wt % NHPI was added with a syringe pump at a rate of 30 cc/hour, in 20 minutes. GC samples were collected after 1, 3, 6, 10, 20 and 30 minutes stirring. The GC samples were clear yellow liquids after filtration to remove the solid catalyst. The process was repeated with sec-butylbenzene hydroperoxide samples containing 0.21 wt % and 0.4 wt % NHPI and the results are shown in FIG. 2.

EXAMPLE 11

Figure 3:
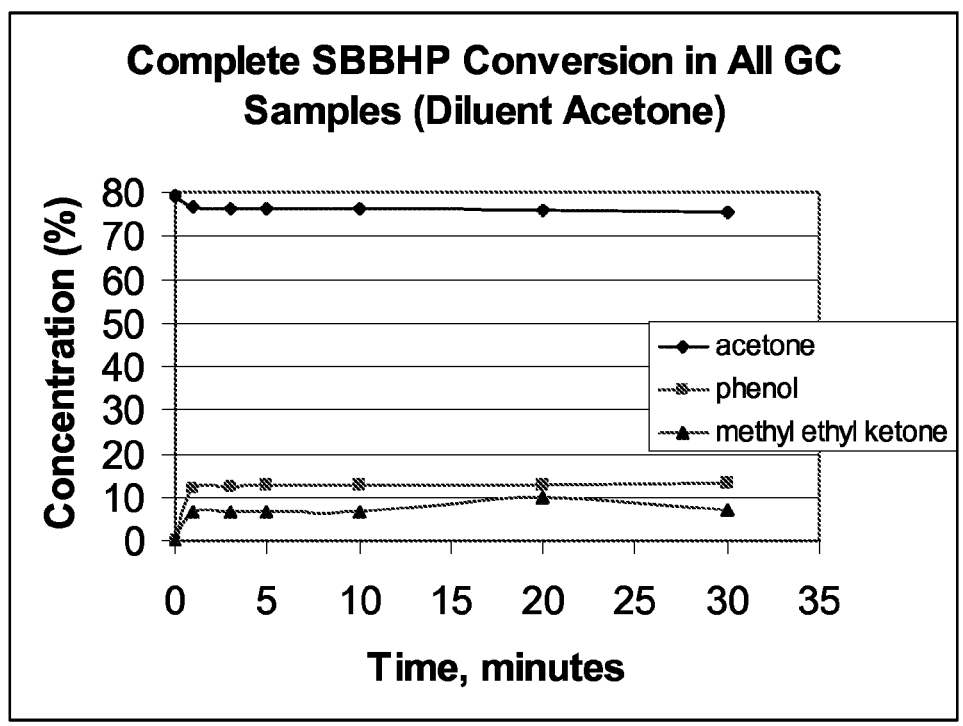
FIG. 3 is a graph of product concentration against time on stream for the cleavage of sec-butylbenzene hydroperoxide in acetone over a Fe/W/Zr oxide catalyst according to the process of Example 11.

Sec-Butyl Hydroperoxide Cleavage Over Fe/W/Zr Oxide Catalyst of Example 5—NHPI Removed from Feed Into a 3-necked 100 ml round bottom flask equipped with an air stirrer, thermometer, chilled water cooled condenser, and nitrogen inductor were added acetone (39.5 g, 50 ml) and 0.5 g of powdered catalyst of Example 5. The acetone and catalyst were heated under acetone reflux (56° C.) and, while refluxing, 10 cc (10.42 g) of 70 wt. % sec-butylbenzene hydroperoxide concentrate (NHPI was removed by caustic wash with dilute $Na_2CO_3$ solution) was added with a syringe pump at a rate of 30 cc/hour, in 20 minutes. The temperature in the reactor rose to 59° C. during this addition period. GC samples were collected after 1, 3, 6, 10, 20 and 30 minutes stirring. The GC samples were clear yellow liquids after filtration to remove the solid catalyst. The results are shown in FIG. 3, from which it will be seen that there was substantially complete conversion of the sec-butylbenzene hydroperoxide to phenol and methyl ethyl ketone.

EXAMPLE 12

Figure 4:
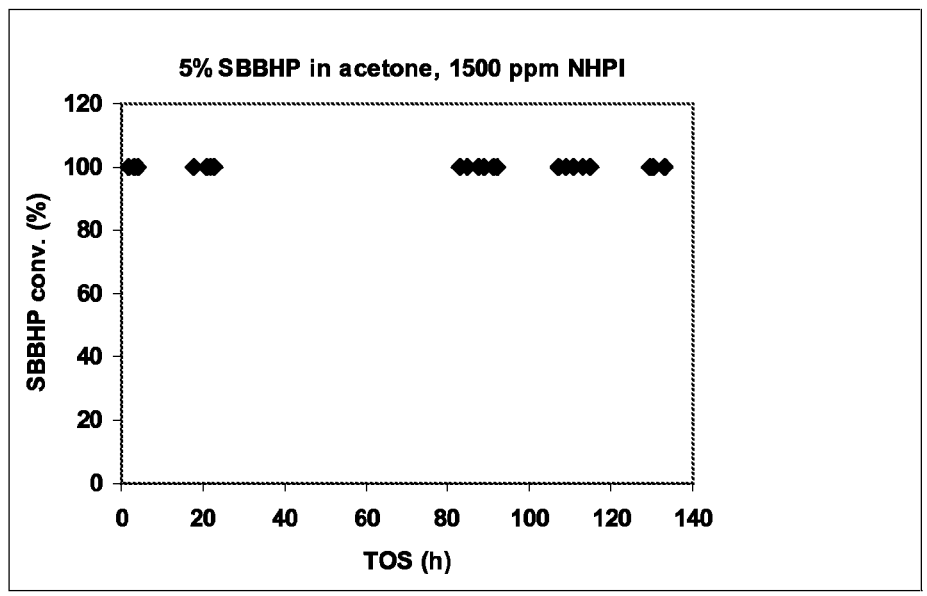
FIG. 4 is a graph of sec-butylbenzene hydroperoxide conversion against time on stream for the cleavage of an acetone solution of sec-butylbenzene hydroperoxide containing 1500 ppm of N-hydroxyphthalimide over a W/Zr oxide catalyst according to the process of Example 12.
Figure 5:
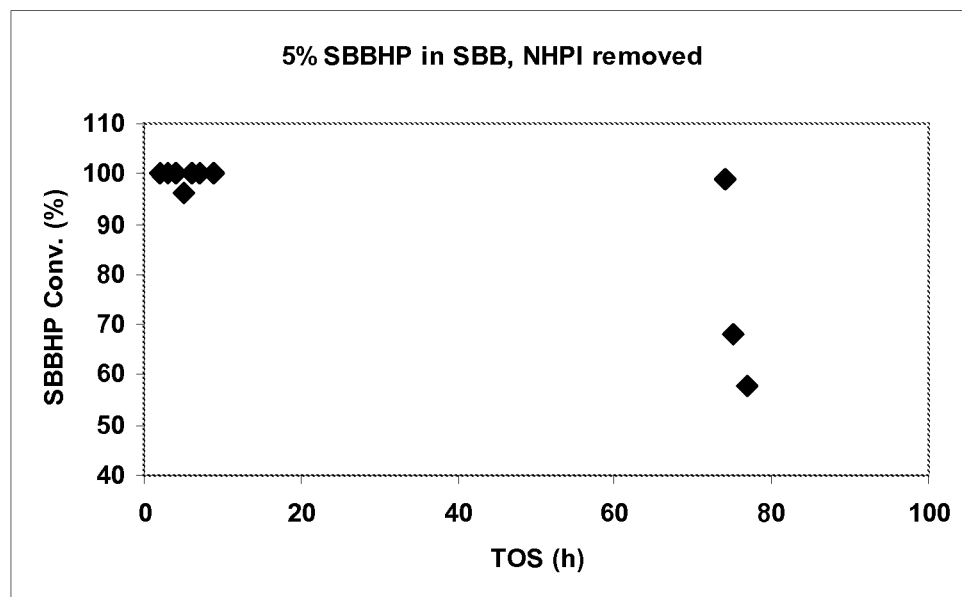
FIG. 5 is a graph of sec-butylbenzene hydroperoxide conversion against time on stream for the cleavage of sec-butylbenzene hydroperoxide diluted with sec-butyl benzene and containing <30 ppm of N-hydroxyphthalimide over a W/Zr oxide catalyst according to the process of Example 13.
Figure 6:
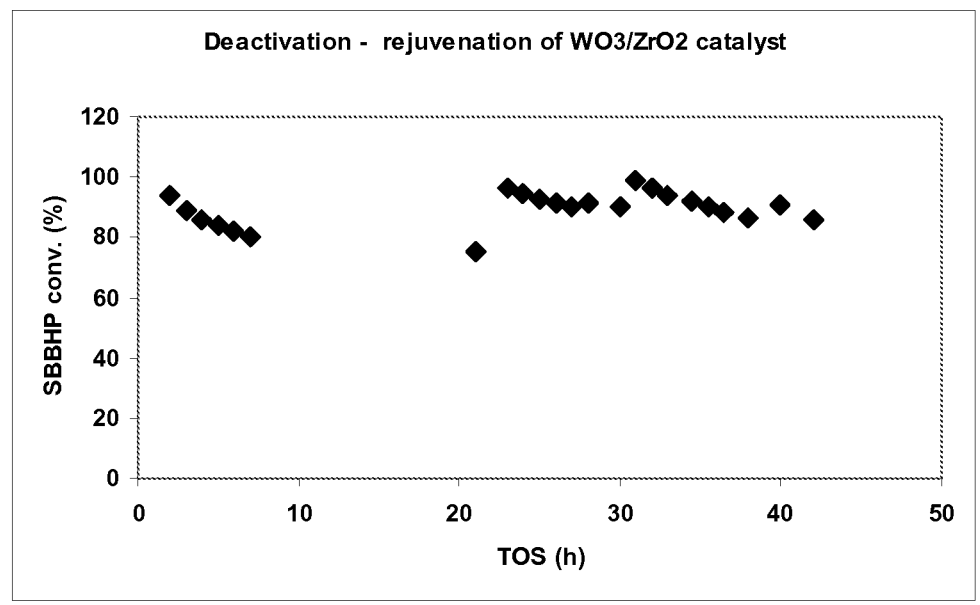
FIG. 6 is a graph of sec-butylbenzene hydroperoxide conversion against time on stream for the cleavage of sec-butylbenzene hydroperoxide diluted with sec-butyl benzene and containing 210 ppm of N-hydroxyphthalimide over a W/Zr oxide catalyst according to the process of Example 14 and after rejuvenation according to the process of Example 15.

Sec-Butyl Hydroperoxide Cleavage Over W/Zr Oxide Catalyst of Example 4-5% SBBHP in Acetone CONTAINING 1500 ppm NHPI The catalyst (1.5 g) prepared in Example 4 was pelletized to 40-80 mesh size, mixed with 60-80 mesh sand (v/v 1:1), and loaded into a ¼-inch diameter stainless steel tubular reactor. The reactor was held at 70° C. and liquid acetone was passed through the reactor tube at 3 cc/min via an ISCO pump for 30 min. The acetone feed was turned off and a 5 wt % solution of sec-butylbenzene hydroperoxide (SBBHP) in acetone containing 1500 ppm NHPI was passed through the reactor via another ISCO pump at a rate of 0.5 cc/min. The products were collected in a chilled knock-out pot and sampled for GC analysis periodically. The results are shown in FIG. 4. No sign of catalyst deactivation was seen even after 130 hours of time on stream.

EXAMPLE 13

Sec-Butyl Hydroperoxide Cleavage Over W/Zr Oxide Catalyst of Example 4—5% SBBHP in SBB with NHPI Removed The catalyst (1.5 g) prepared in Example 4 was pelletized to 40-80 mesh size, mixed with 60-80 mesh sand (v/v 1:1), and loaded into a ¼-inch diameter stainless steel tubular reactor. The reactor was held at 70° C. and liquid acetone was passed through the reactor tube at 3 cc/min via an ISCO pump for 30 min. The acetone feed was turned off and a 5 wt % solution of sec-butylbenzene hydroperoxide (SBBHP) in sec-butylbenzene (SBB) containing <30 ppm NHPI was passed through the reactor via another ISCO pump at a rate of 0.25 cc/min. The products were collected in a chilled knock-out pot and sampled for GC analysis periodically. The results are shown in FIG. 3, from which it will be seen that the catalyst started to deactivate after about 70 hrs time on stream, as indicated by the decrease of SBBHP conversion.

EXAMPLE 14

Sec-Butyl Hydroperoxide Cleavage Over W/Zr Oxide Catalyst of Example 4—5% SBBHP in SBB/Acetone Containing 310 ppm NHPI The catalyst (1.5 g) prepared in Example 4 was pelletized to 40-80 mesh size, mixed with 60-80 mesh sand (v/v 1:1), and loaded into a ¼-inch diameter stainless steel tubular reactor. The reactor was held at 70° C. and liquid acetone was passed through the reactor tube at 3 cc/min via an ISCO pump for 30 min. The acetone feed was turned off and a 5 wt % solution of SBBHP in 98/2 (wt/wt) SBB/acetone containing 310 ppm NHPI was passed through the reactor via another ISCO pump at a rate of 0.25 cc/min. The products were collected in a chilled knock-out pot and sampled for GC analysis periodically. The results are shown in FIG. 4, from which it will be seen that the catalyst started to deactivate after about 2 hrs time on stream.

EXAMPLE 15

Rejuvenation of Deactivated W/Zr Oxide Catalyst of Example 14 Using Acetone Solvent The rejuvenation was carried out in-situ as part of the experiment in Example 14. Once the SBBHP conversion dropped to below 80%, the hydroperoxide feed containing NHPI was turned off While maintaining the reactor at 70° C., acetone was passed through the catalyst bed at 3 cc/min for a period of 30 min. Then the acetone flow was stopped and the hydroperoxide feed was resumed. The catalyst activity was regained as indicated by the increase in SBBHP conversion back to almost 100%. Such deactivation-rejuvenation cycles were performed three times (FIG. 4), with the initial catalyst activity being substantially regained after each rejuvenation cycle.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing phenol or a substituted phenol, the process comprising contacting cyclohexylbenzene hydroperoxide with a first catalyst comprising an oxide of at least one metal from Groups 3 to 5 and Groups 7 to 14 of the Periodic Table of the Elements and an oxide of at least one metal from Group 6 of the Periodic Table of the Elements.

2. The process of claim 1, wherein the first catalyst comprises an oxide of at least one metal from Group 4 of the Periodic Table of the Elements and an oxide of at least one metal from Group 6 of the Periodic Table of the Elements.

3. The process of claim 1, wherein the first catalyst comprises zirconium oxide and an oxide of at least one of molybdenum and tungsten.

4. The process of claim 2, wherein the first catalyst further comprises an oxide of at least one metal from Groups 8 to 11 of the Periodic Table of the Elements.

5. The process of claim 2, wherein the first catalyst further comprises an oxide of at least one of iron and copper.

6. The process of claim 1, wherein said contacting is conducted at a temperature of 40° C. to 120° C., a pressure of 100 to 1000 kPa, and a liquid hourly space velocity (LHSV) based on the hydroperoxide of 1 to 50 $hr^{-1}$.

7. The process of claim 1, wherein said cyclohexylbenzene hydroperoxide is produced by oxidizing cyclohexylbenzene with an oxygen-containing gas in the presence of a second catalyst comprising a cyclic imide having a general formula (III):

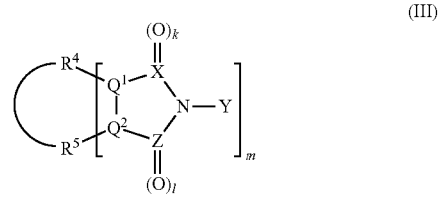

wherein each of $R^4$ and $R^5$ is independently selected from hydrocarbyl and substituted hydrocarbyl radicals having 1 to 20 carbon atoms, or from the groups $SO_3H$, $NH_2$, OH, and $NO_2$ or from the atoms H, F, Cl, Br, and I, provided that $R^4$ and $R^5$ can be linked to one another via a covalent bond;
each of $Q^1$ and $Q^2$ is independently selected from C, CH, N, $CR^6$;
each of X and Z is independently selected from C, S, $CH_2$, N, P and elements of Group 4 of the Periodic Table;
Y is O or OH;

k is 0, 1, or 2;
l is 0, 1, or 2;
m is 1 to 3; and
$R^6$ can be any of the entities listed for $R^4$.

8. The process of claim 7, wherein said cyclic imide obeys the general formula (IV):

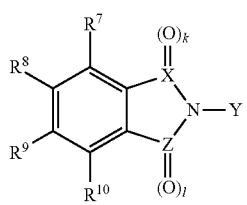

(IV)

wherein each of $R^7$, $R^8$, $R^9$, and $R^{10}$ is independently selected from hydrocarbyl and substituted hydrocarbyl radicals having 1 to 20 carbon atoms, or from the groups $SO_3H$, $NH_2$, OH, and $NO_2$ or from the atoms H, F, Cl, Br, and I,
each of X and Z is independently selected from C, S, $CH_2$, N, P and elements of Group 4 of the Periodic Table;
Y is O or OH;
k is 0, 1, or 2; and
l is 0, 1, or 2.

9. The process of claim 7, wherein said cyclic imide comprises N-hydroxyphthalimide.

10. The process of claim 7, wherein said oxidizing produces an effluent comprising said alkylaromatic hydroperoxide and unreacted cyclic imide catalyst and the process further comprises treating said effluent prior to said contacting to remove at least part of the unreacted cyclic imide catalyst in said effluent.

11. The process of claim 10, wherein said treating comprises contacting said effluent with an aqueous solution of a base to produce an aqueous phase comprising at least part of said unreacted imide catalyst and an organic phase comprising said alkylaromatic hydroperoxide.

12. The process of claim 11, wherein said effluent is contacted with an aqueous solution of a weak base having a pKb value greater than or equal to the pKa value of the cyclic imide.

13. The process of claim 11, wherein said effluent is contacted with an aqueous solution of at least one of a metal carbonate and hydrogen carbonate.

14. The process of claim 10, wherein said treating comprises contacting said effluent with a solid sorbent.

15. The process of claim 14, wherein said solid sorbent comprises at least one of a metal oxide, a metal carbonate and/or hydrogen carbonate, a clay, and an ion exchange resin.

16. The process of claim 14, wherein said solid sorbent comprises a metal oxide having a molar ratio of chemisorption of $CO_2$ per gram of metal oxide to the chemisorption of $NH_3$ per gram of metal oxide greater than 0.5.

17. The process of claim 1, wherein said alkylaromatic hydroperoxide is dissolved in a polar solvent, prior to said contacting.

18. The process of claim 1, and further comprising periodically rejuvenating said first catalyst by washing the first catalyst with a polar solvent.

* * * * *